(12) United States Patent
Hengerer et al.

(10) Patent No.: US 8,208,987 B2
(45) Date of Patent: Jun. 26, 2012

(54) METHOD AND DEVICE FOR QUANTIFYING THE UPTAKE OF AT LEAST ONE RADIOTRACER IN A BODY REGION OF A PATIENT OF INTEREST TO A POSITRON EMISSION TOMOGRAPHY MEASUREMENT

(75) Inventors: Arne Hengerer, Erlangen (DE); Ralph Strecker, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1160 days.

(21) Appl. No.: 12/222,923

(22) Filed: Aug. 20, 2008

(65) Prior Publication Data

US 2009/0117044 A1    May 7, 2009

(30) Foreign Application Priority Data

Aug. 21, 2007  (DE) .......................... 10 2007 039 454

(51) Int. Cl.
*A61B 5/00* (2006.01)
(52) U.S. Cl. ........ 600/411; 600/436; 600/420; 600/427; 250/303; 250/356.2; 250/363.04; 250/363.03; 250/363.02; 250/260
(58) Field of Classification Search ............... 424/9.1, 424/9.3, 9.4, 179.1; 600/436, 411, 431, 420, 600/416, 427; 382/128, 130, 131; 250/363.04, 250/363.03, 363.01, 363.02, 362, 260, 303, 250/356.2
See application file for complete search history.

(56) References Cited

U.S. PATENT DOCUMENTS

| | | | | |
|---|---|---|---|---|
| 6,009,342 A * | 12/1999 | Brasch et al. | ................. | 600/420 |
| 7,069,068 B1 * | 6/2006 | Ostergaard | .................... | 600/420 |
| 7,627,360 B2 * | 12/2009 | Kimura | ......................... | 600/419 |
| 2006/0284096 A1 | 12/2006 | Krieg et al. | | |
| 2007/0230757 A1 * | 10/2007 | Trachtenberg et al. | ....... | 382/128 |
| 2008/0014149 A1 * | 1/2008 | Murthy et al. | ............... | 424/9.36 |

FOREIGN PATENT DOCUMENTS

DE    10 2005 023 906.4    11/2006

OTHER PUBLICATIONS

Huafeng Liu et al., Robust reconstruction of physiological parameters from dynamic PET data $4^{th}$ International Symposium on Biomedical Imaging: From Nano to Macro, Apr. 12-15, 2007, 177-180.

* cited by examiner

*Primary Examiner* — Brian Casler
*Assistant Examiner* — Amanda Lauritzen
(74) *Attorney, Agent, or Firm* — Harness, Dickey & Pierce, P.L.C.

(57) ABSTRACT

A method for quantifying the uptake of at least one radiotracer in a body region of a patient of interest to a positron emission tomography measurement is disclosed. In at least one embodiment of the method, the uptake of the radiotracer in the body region of the patient of interest to the positron emission tomography measurement is quantified taking into account at least one permeability information item relating to the permeability of at least one blood vessel of the patient, in particular in the body region of interest.

21 Claims, 2 Drawing Sheets

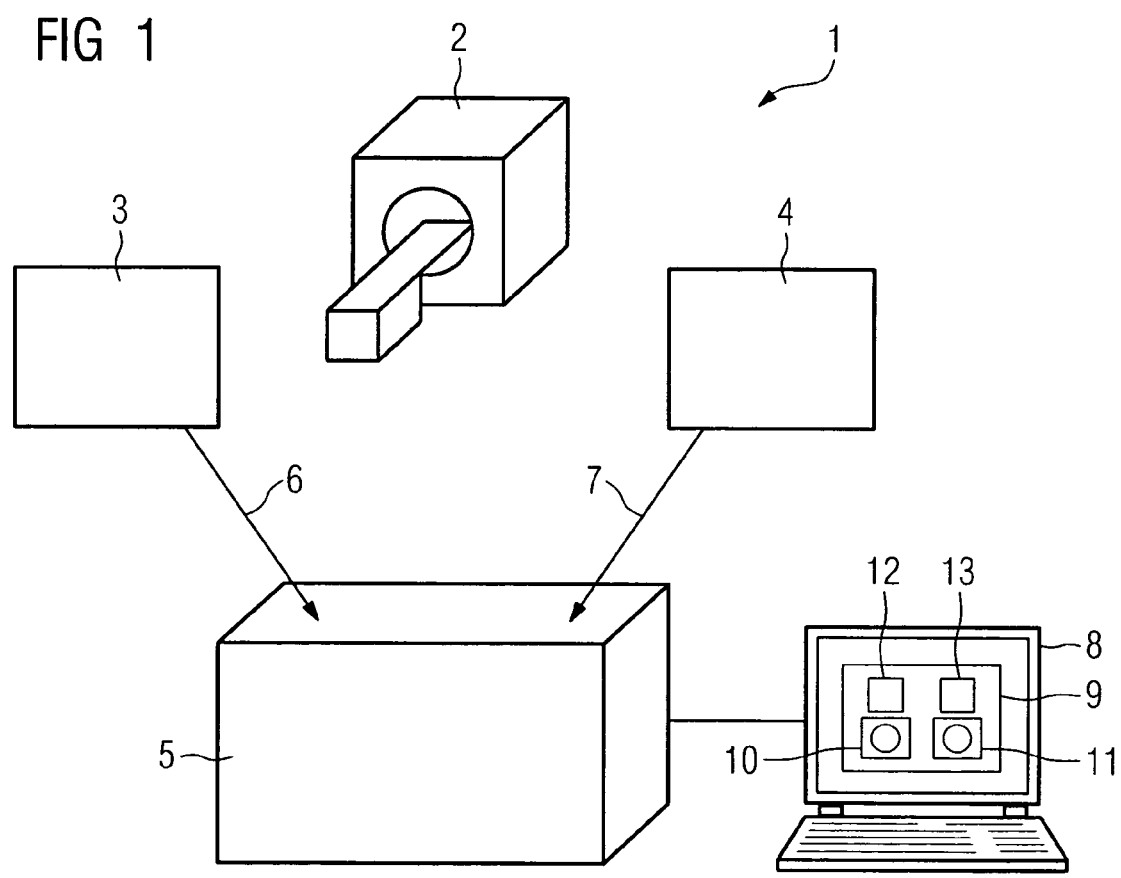

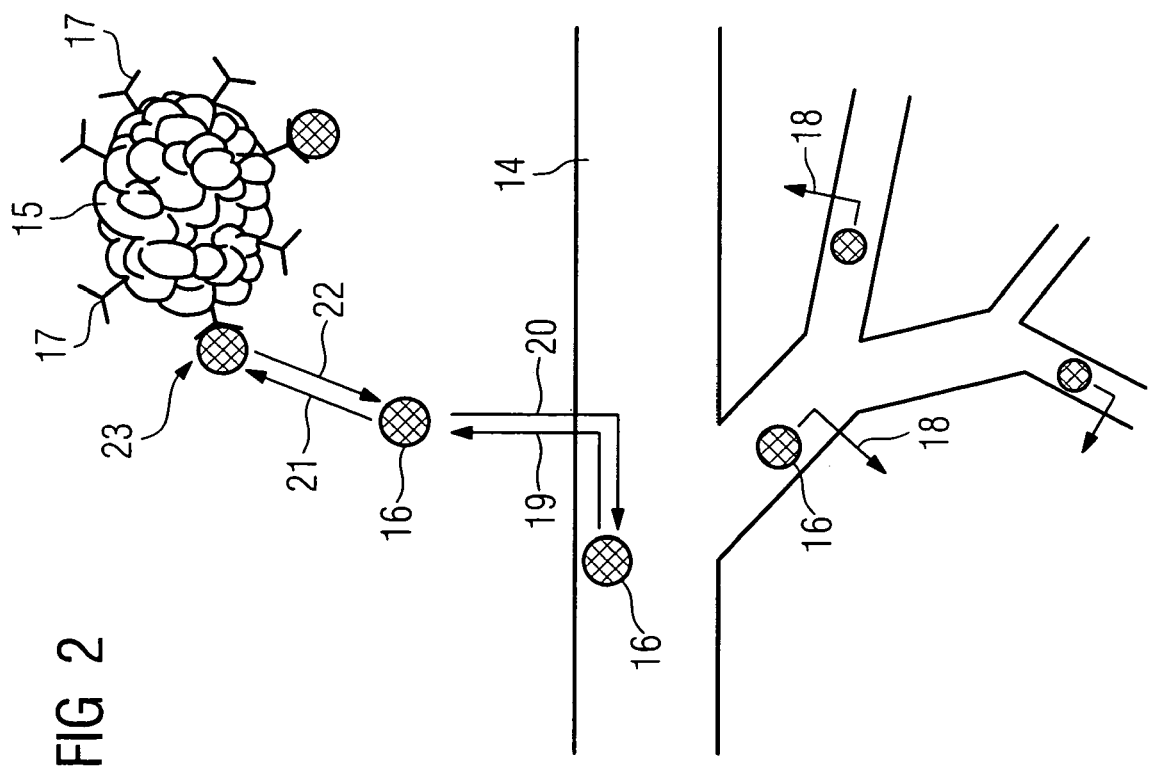

METHOD AND DEVICE FOR QUANTIFYING THE UPTAKE OF AT LEAST ONE RADIOTRACER IN A BODY REGION OF A PATIENT OF INTEREST TO A POSITRON EMISSION TOMOGRAPHY MEASUREMENT

PRIORITY STATEMENT

The present application hereby claims priority under 35 U.S.C. §119 on German patent application number DE 10 2007 039 454.5 filed Aug. 21, 2007, the entire contents of which is hereby incorporated herein by reference.

FIELD

Embodiments of the invention generally relate to a method for quantifying the uptake of at least one radiotracer in a body region of a patient of interest to a positron emission tomography measurement.

BACKGROUND

So-called radiopharmaceuticals or radiotracers, which are substances marked with a radionuclide, are used for imaging in the field of positron emission tomography. These radiotracers are usually administered to the patient by means of an injection, or possibly using another method. Positrons are emitted when the radionuclides decay and respectively interact with one electron. These two particles annihilate as a result of this interaction, so that high-energy photons are created which can be detected as annihilation radiation.

F-18-fluoro-2-deoxyglucose (F-18-FDG) is a typical radiotracer used in positron emission tomography. Positron emission tomography studies (PET-studies) using this tracer and different radiotracers are used for example to monitor therapy progress in the case of gastrointestinal stromal tumors (GIST) inter alia, by way of example after therapy using Imatinib. Therapy monitoring by means of PET permits early detection of possible therapy failures or insufficient dosage by precisely quantifying the metabolism as it progresses.

However, it is unclear whether (possibly determined) reduced uptake of a radiotracer in a tissue or body region is due to a metabolic change during the progress of the therapy, or whether it is due to changed receptor expression in a pathology and/or whether hypoperfusion is present. Such uncertainty exists mainly in therapies combined with anti-angiogenesis (for example, in therapy regimes whose starting point is the vascular endothelial growth factor (VEGF) signal molecule), but also in other therapy regimes such as radiation therapy, for example.

Huafeng L. et al., in "Robust reconstruction of physiological parameters from dynamic PET data", $4^{th}$ IEEE International Symposium on Biomedical Imaging: From Nano to Macro, Apr. 12-15, 2007, 177-180 disclose a model for quantifying physiological and biological processes by means of PET. The state variable inputs of this model are the concentration of the radiotracer in the individual compartments of the tissue such as blood, extracellular space, the volume of the cells and the exchange rate between the compartments. Appropriate measurement models are used to determine the parameters. Flow rates and exchange rates are obtained by appropriate compartmenting of the PET measurement data. The rates of the radiotracer flow from the tissue to the blood, and vice versa, are determined from PET measurements.

DE 10 2005 023 906 A1 discloses a method for determining positron emission measurement information in which a second imaging method for determining perfusion and/or diffusion information is used at the same time as the positron emission tomography generates image records. A contrast agent can also be used for this purpose.

Correctly quantifying the local tracer uptake is important for quantitative evaluation of the pharmacokinetics in the case of dynamic PET studies (tracer kinetic modeling). For this purpose, the acquired raw data has to be corrected in a number of ways, for example for photon scattering in the patient and in the PET detector and for photon absorption. The quantified values for the various tracers are generally specified as so-called standardized uptake values (SUVs). However, the corrections undertaken are limited and are insufficient in particular with regard to the quantification problems described initially.

SUMMARY

In at least one embodiment, a method is specified for quantifying the uptake of at least one radiotracer in a body region of a patient of interest to a positron emission tomography measurement.

In at least one embodiment, in a method of this type, the uptake of the radiotracer in the body region of the patient of interest to the positron emission tomography measurement is quantified taking into account at least one permeability information item relating to the permeability of at least one blood vessel of the patient, in particular in the body region of interest.

According to at least one embodiment of the invention, the correction thus takes place taking into account the permeability of the vessel. Quantification thus takes place (amongst other things in general) depending on data relating to the transfer of the radiotracer, or of substances in general, from the blood vessels into the surrounding tissue. The substance exchange can thus be included quantitatively in determining the uptake of the radiotracer in the tissue, so that it is possible to draw conclusions with regard to the vascularization or the vessel permeability with regard to the transfer into the tissue.

A computational device, which can be a control device for controlling, inter alia, the recording of the PET data, preferably takes into account the uptake of the radiotracer, or, in general, quantifies it.

It is essential for the method according to at least one embodiment of the invention that actual permeability data, that is to say data relating to the transfer from the vessel system to the tissue, is obtained rather than data which only, for example, relates to perfusion, that is to say the blood supply in the vessels, or diffusion, that is to say the substance distribution in the tissue.

Hence, according to at least one embodiment of the invention, by taking into account the permeability when quantifying the tracer uptake, a significant evaluation of therapy monitoring of a patient possible by means of PET is carried out in order to recognize therapy failure or to correct a dosage, etc.

In particular, at least one permeability information item can be determined within the scope of a dynamic contrast enhanced magnetic resonance imaging measurement. In the case of the dynamic contrast enhanced magnetic resonance imaging measurement (DCE-MRI measurement) a series of magnetic resonance images are recorded, with the images being recorded at least in part after the administration of a contrast agent.

The uptake of the radiotracer can be quantified by taking into account the different permeability of a contrast agent used for magnetic resonance imaging and of the radiotracer and/or by taking into account the relaxivity of the contrast agent. What is taken into account is that for example a contrast agent for DCE-MRI has different permeability data than the radiotracer used in the PET. By way of example, the permeability can be determined within the scope of an experiment. The discrepancies between the experimental data and/or the values of the permeability of the contrast agent and the radiotracer can be recorded as correction factors, or as a single (if appropriate combined) correction factor, which is then included in the algorithm for determining the uptake of the radiotracer in the pathology or the tissue. Using this, a direct measurement or absolute quantification is possible in which magnetic resonance signals are converted into concentration values, with the relaxivity as a contrast agent specific substance constant being used in the conversion, the value of which in the tissue is unknown at first or can only be estimated. The relaxivity of the contrast agent can differ by up to 50% from the blood plasma in different tissue types, with the dependence being a function of the proportion of macromolecules such as proteins. The correspondingly different permeability data and permeability information and/or relaxivity values for the contrast agent can be taken into account by way of correction factors or correction measurements.

Advantageously, a standardized uptake value is determined within the scope of quantifying the uptake of the radiotracer in the body region of interest. This standardized uptake value can be the known standardized uptake value (SUV). Such quantification for determining a standardized uptake value can also be carried out largely automatically by a computational device or a control device which records the measurement data or carries out the examination. By way of example, for this purpose, program means or else a program package can be installed on a control device for the PET which, where appropriate, not only automatically records the measurement data but also evaluates it automatically or with user support and, as a result, outputs information regarding the standardized uptake value with further information which can possibly be accessed separately where appropriate. The description as standardized uptake value allows reproducing in a comparable manner the local tracer uptake and evaluating it. Quantitative evaluation of the pharmacokinetics is thus possible.

At least one permeability information item can be determined within the scope of a magnetic resonance imaging measurement. Of course it is possible to use other methods or measurements rather than, or possibly in addition to, magnetic resonance imaging measurements to obtain permeability information. However, magnetic resonance imaging is particularly suitable for obtaining permeability information due to its high temporal resolution compared to PET.

At least one macromolecular substance can be used as a contrast agent, in particular iron oxide nanoparticles and/or at least one nanoscale gadolinium assembly. Examples of contrast agents for DEC-MRI include superparamagnetic iron oxides (SPIOs), monocrystalline iron oxides (MIONs) and very small iron oxide particles (VSOPs) as iron oxide nanoparticles and gadolinium loaded micelles as nanoscale gadolinium assemblies. Further examples include the clinically approved low-molecular gadolinium complexes (such as Gd-DTPA, i.e. Gd-diethylene triamine pentaacetic acid).

Advantageously, magnetic resonance imaging data is recorded before, during and after the administration of a contrast agent and/or information relating to at least one native tissue signal, contrast agent enhancement in at least one blood vessel and contrast agent enhancement in at least a part of the body region of interest is determined from the recorded magnetic resonance imaging data. In this case, the magnetic resonance data can in principle be recorded by a hybrid modality, that is to say by an integrated MRI/PET device. This is advantageous because no repositioning of the patient is required and both measurements can, at least in part, be taken simultaneously. Errors occurring due to co-registration, image fusion and the like are thus avoided.

It should be noted that the method of at least one embodiment is limited to extracranial examinations due to the blood-brain barrier, or to therapy monitoring in the case of neuronal tumors with blood-brain barrier defects. In this case at least one embodiment of the method does not relate to the therapy itself, but to the measurement of physical or chemical measurement data and physiological parameters, or, primarily, their evaluation. In this context, intervention by a medical practitioner is not necessary. The measurement data is rather recorded automatically by a control or computational device of an integrated PET/MRI machine for example, and evaluated automatically as far as possible, assisted by an operator of such a machine where appropriate. Such machines are generally operated by technical staff, for example medical technical assistants or scientists.

The magnetic resonance contrast agents leave the interstitial space through the vessel walls as a function of their molecular weight. The basis of the dynamic contrast enhanced magnetic resonance imaging is the acquisition of a series of magnetic resonance images generally before, during and after (usually intravenous) administration of a contrast agent. The signal intensity in the magnetic resonance images includes the native tissue signal, that is to say the signal without the administration of contrast agents, the contrast enhancement in the blood vessels and the contrast enhancement in the tissue. Various measurement information items can be obtained therefrom, for example relating to the substance exchange. The correspondingly obtained information can be displayed quantitatively in the magnetic resonance image for an improved overview for an operator, for example. This permits conclusions about the vessel supply, for example in pathological areas as body regions of the patient of interest.

The uptake of the radiotracer in the body region of interest for the positron emission tomography measurement can be quantified on the basis of at least one pharmacokinetic model, in particular using the Brix model and/or the Kety (Tofts) model and/or an extended Kety model. Such pharmacokinetic modeling, carried out using single, differing models or using a combination of models, makes it possible to determine various parameters which permits conclusions regarding the degree of vascularization and vessel permeability, for example, and thus allows a standardized uptake value to be corrected. Modeling using different models can be carried out in parallel, where appropriate, in order to make comparisons between the results of the different models or obtain more accurate end data by forming averages and the like. The mentioned pharmacokinetic models are understood to be merely exemplary. Of course it is possible to use different models, or models that have been adapted with regard to these basic models. The Kety model is occasionally also referred to as the Tofts model.

Within the scope of pharmacokinetic modeling at least one kinetic substance exchange constant and/or one extracellular volume fraction and/or at least one further modeling value can be determined allowing conclusions about at least one permeability information item. For example, the kinetic substance exchange constant $K^{trans}$ or the extracellular volume fraction, that is to say the proportion of the substance in the extracellular space, are measured and displayed quantitatively in the magnetic resonance image where appropriate. Of course, within the scope of the pharmacokinetic modeling it is possible to determine further values not explicitly mentioned here and display them on a display where appropriate.

The previously mentioned Kety model is an example of a kinetic model; it satisfies the equation $$C_t(t) = K^{trans} \int_0^t C_p(t') \exp\left(\frac{-K^{trans}(t-t')}{v_e}\right) dt,$$

where $C_t(t)$ relates to the measured concentration of the contrast agent in a body region of interest, for example in the tumor tissue; $C_p$ is the blood plasma concentration of the contrast agent; and $v_e$ represents the extracellular volume fraction. Time is denoted by t. $K^{trans}$ is the previously mentioned kinetic substance exchange constant.

The hematocrit value is expediently estimated to be 0.42.

In an extension of this Kety model, the term $v_p C_p(t)$ as a summand is additionally taken into account, where $C_p$ refers to the blood plasma concentration of the contrast agent, and $v_p$ refers to the overall blood volume.

As was mentioned previously, it is possible that at least one modeling value determined within the scope of the pharmacokinetic modeling is displayed in at least one magnetic resonance image, in particular in quantified form. This may provide an operator, for example a medical technical assistant, a medical practitioner or a scientist, with a quick overview relating to the values relevant for correcting the tracer uptake.

At least one permeability information item can be recorded simultaneously with the positron emission tomography measurement.

Thus, PET data is expediently recorded at the same time as the further data for determining the permeability values, in particular at the same time as the magnetic resonance data created by a magnetic resonance measurement. This allows the data to be directly compared.

The uptake of the radiotracer in the body region of interest can be quantified taking into account at least one further information item, in particular by taking into account the scattering of photons in the body region of interest and/or in a detector used for the positron emission tomography measurement and/or by taking into account the absorption of photons in the body region of interest.

Quantifying the uptake of the radiotracer in general involves taking into account a multiplicity of factors or information items, so that the (corrected) quantification is as precise as possible. That is to say, further correction values are advantageously considered in addition to the permeability so that the uptake of the tracer can be specified as precisely as possible.

The positron emission tomography measurement and at least one permeability information item and/or at least one further information item where appropriate can be recorded using an integrated medical recording device, in particular using an integrated positron emission tomography and magnetic resonance imaging device and/or without repositioning the patient. Such hybrid modalities or integrated modalities provide the advantage that, for example in a control device, it is possible to fall back on measurement protocols provided for a combined record so that there is less effort for the user. Furthermore, repositioning the patient for obtaining or recording different information items can be dispensed with. The measurements can be carried out simultaneously or in parallel. Errors which often occur in the case of co-registration and image fusion of images from different modalities can thus be avoided.

Furthermore, it is possible that at least one permeability information item and/or, where appropriate, at least one further information item is or are taken into account within the scope of correcting a determined uptake of a radiotracer in the body region of interest. In this case, vessel permeability is hence taken into account by determining a correction factor or by correcting an initially recorded uptake of the radiotracer in a region of a tumor, for example.

Moreover, the uptake of a therapeutic pharmaceutical as a radiotracer can be quantified. Therapeutic pharmaceuticals such as chemotherapeutic agents or radioactively marked antibodies are thus used as radiotracers and their interstitial enhancement is determined depending on the degree of vascularization. Thus, trials of diagnostic pharmaceuticals (for PET) can be supported with the aid of the method described above by determining enhancement in the target tissue independently of the vascularization.

As was mentioned above, it is possible that the uptake of the radiotracer in the body region of interest to the positron emission tomography measurement is quantified within the scope of monitoring the course of a therapy, in particular a tumor treatment. Of course it is likewise possible that quantifying the uptake of the radiotracer according to the invention is used for other purposes. However, in tumor therapy it is particularly important to correct or determine a standardized uptake value in particular according to the invention because in this case there is a considerable uncertainty with regard to the influences or occurrences of hypoperfusion or a changed metabolism in the case of changed receptor expressions and the like, primarily in the case of therapies based on preventing new vessels from being formed.

Furthermore, the application relates to a medical device designed to carry out at least one embodiment of the method described above.

BRIEF DESCRIPTION OF THE DRAWINGS

Further advantages, features and details of the invention emerge from the following example embodiments and from the drawings, in which FIG. 1 shows a schematic diagram for carrying out a method according to an embodiment of the invention, and FIGS. 2 and 3 show sketches for using a method according to an embodiment of the invention within the scope of tumor therapy.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another.

For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially; relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a schematic diagram for carrying out a method according to an embodiment of the invention.

In this case, a medical device 1 according to an embodiment of the invention, including an integrated unit 2 for recording PET data and magnetic resonance data in particular within the scope or DCE-MRI, records PET data in accordance with the box 3 and magnetic resonance data in accordance with the box 4.

The medical device 1 furthermore includes a computational device 5 which is fed PET data and MRI data according to boxes 3 and 4, this being indicated by arrows 6 and 7. The use of the MRI data according to box 4 makes it possible to quantify the uptake of the radiotracer for the PET by taking into account the permeability information obtained from the MRI data and further data in order to obtain a corrected standardized uptake value for the uptake of the radiotracer in the tissue. The computational device 5 calculates or determines this standardized uptake value (preferably automatically, at least for the most part). The medical device 1 furthermore comprises a screen 8 for operator support, with input means such as keyboards and the like being connected thereto in order to enable inputs by an operator, such as a medical technical assistant, medical practitioner or scientist.

A surface 9 of a DCE-MRI image is sketched on the screen 8. First of all, a magnetic resonance image 10 is recorded in parallel with the PET measurement. Kinetic substance exchange constants and values for the extracellular volume fraction of the contrast agent or the radiotracer are determined from further magnetic resonance images, which are not illustrated in this case and which were created before, during and after an intravenous contrast agent was administered to a patient (not shown), and are displayed in a correspondingly adapted magnetic resonance image 11. Selection of the desired measurement sequences for the magnetic resonance images is carried out via box 12. Box 13 displays as text the substance exchange constants, the extracellular volume fraction or a standardized uptake value for the radiotracer or displays calculated and measured curves of the aforementioned, or for the aforementioned.

Of course the surface 9 can also be displayed differently, for example depending on user specifications.

FIGS. 2 and 3 show sketches for using a method according to an embodiment of the invention within the scope of tumor therapy.

FIG. 2 shows the situation before therapy. The contrast agent for magnetic resonance imaging carried out to obtain permeability information and anatomical data is in this case used as a therapeutic agent. A vessel 14 in the body region of interest—in this case in the region of a tumor 15—which has different branches in the form of neovascular structures is illustrated. Furthermore, different contrast agent particles 16 can be seen, which are in part still located in the vessel 14 and in part are already located in the tissue area or at the receptors 17 of the tumor 15.

The transfer of the contrast agent particles 16 for DCE magnetic resonance imaging from the blood vessel 14 into the surrounding tissue is indicated by the arrows 18.

The corresponding rates of transfer of a contrast agent particle 16 into the tissue according to arrow 19, or back into the vessel according to arrow 20, are given by the substance constant $K^{trans}$, or by the substance constant $K^{trans}$ divided by the extracellular volume fraction of the contrast agent.

The docking process onto the tumor 15 (according to arrows 21 and 22) to form a complex 23 comprising a receptor 17 and a contrast agent particle 16 is determined by the ratio of the two rates according to arrows 21 and 22. This ratio is obtained by dividing the concentration of the complex 23 of the receptor and contrast agent by the sum of the concentrations of the contrast agent and receptors 17.

FIG. 3 indicates the situation after therapy. The tumor 15 which now has fewer receptors 17 can again be seen. There is no branching from the vessel 14, that is to say there is no neovascular structure. This leads to a correspondingly limited substance exchange rate, indicated in this case by arrows 24 and 25. The docking process onto the tumor occurs at the rates according to arrows 26 and 27. Hence, after therapy there is a significant change in the ratios relating to the vessel permeability of the vessel 14 compared to the state before therapy, and hence there are correspondingly different permeability information items.

The changed situation, that is to say for example the decreased concentration at the receptors 17 after therapy or the reduced $K^{trans}$ value are, according to an embodiment of the invention, included when determining the standardized uptake value for the radiotracer so that a quantitatively exact evaluation is possible. By way of example, by these means it can be determined without doubt that a changed permeability figures in the changed uptake of a radiotracer.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDS; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for quantifying uptake of at least one radiotracer in a body region of a patient of interest to a positron emission tomography measurement, the method comprising:

quantifying the uptake of the at least one radiotracer in the body region of the patient of interest to the positron emission tomography measurement
by taking into account at least one permeability information item relating to permeability of at least one blood vessel of the patient determined within the scope of a dynamic contrast-enhanced magnetic resonance imaging measurement, and
by taking into account differing permeability of an used contrast agent for magnetic resonance imaging and at least one of the permeability of the at least one radiotracer and relaxivity of the contrast agent,
wherein the quantifying occurs based on data relating to the transfer of the at least one radiotracer from the at least one blood vessel of the patient into tissue surrounding the body region.

2. The method as claimed in claim 1, wherein a standardized uptake value is determined within the scope of quantifying the uptake of the at least one radiotracer in the body region of interest.

3. The method as claimed in claim 1, wherein at least one macromolecular substance is used as a contrast agent.

4. The method as claimed in claim 1, wherein at least one of magnetic resonance imaging data is recorded before, during and after the administration of a contrast agent, and information relating to at least one native tissue signal, contrast agent enhancement in at least one blood vessel and contrast agent enhancement in at least a part of the body region of interest is determined from the recorded magnetic resonance imaging data.

5. The method as claimed in claim 1, wherein the uptake of the at least one radiotracer in the body region of interest for the positron emission tomography measurement is quantified on the basis of at least one pharmacokinetic model.

6. The method as claimed in claim 5, wherein, within the scope of the at least one pharmacokinetic modeling, at least one of the following is determined, allowing conclusions about at least one permeability information item:
at least one kinetic substance exchange constant,
one extracellular volume fraction, and
at least one further modeling value.

7. The method as claimed in claim 1, wherein least one modeling value determined within the scope of pharmacokinetic modeling is displayed in at least one magnetic resonance image.

8. The method as claimed in claim 1, wherein the at least one permeability information item is recorded simultaneously with the positron emission tomography measurement.

9. The method as claimed in claim 1, wherein the uptake of the at least one radiotracer in the body region of interest is quantified taking into account at least one further information item.

10. The method as claimed in claim 9, wherein the positron emission tomography measurement and at least one of the at least one permeability information item and the at least one further information item where appropriate is recorded using an integrated medical recording device.

11. The method as claimed in claim 9, wherein the at least one of at least one permeability information item and, where appropriate, the at least one further information item is taken into account within the scope of correcting a determined uptake of the at least one radiotracer in the body region of interest.

12. The method as claimed in claim 1, wherein the uptake of a therapeutic pharmaceutical as the at least one radiotracer is quantified.

13. The method as claimed in claim 1, wherein the uptake of the at least one radiotracer in the body region of interest to the positron emission tomography measurement is quantified within the scope of monitoring the course of a therapy.

14. The method as claimed in claim 3, wherein the at least one macromolecular substance includes at least one of iron oxide nanoparticles, at least one nanoscale gadolinium assembly and at least one low-molecular gadolinium complex.

15. The method as claimed in claim 2, wherein at least one macromolecular substance is used as a contrast agent.

16. The method as claimed in claim 15, wherein the at least one macromolecular substance includes at least one of iron oxide nanoparticles, at least one nanoscale gadolinium assembly and at least one low-molecular gadolinium complex.

17. The method as claimed in claim 5, wherein the uptake of the at least one radiotracer in the body region of interest for the positron emission tomography measurement is quantified on the basis of the at least one pharmacokinetic model using at least one of a Brix model, a Kety model and an extended Kety model.

18. The method as claimed in claim 17, wherein, within the scope of the at least one pharmacokinetic model, at least one of the following is determined, allowing conclusions about at least one permeability information item:
   at least one kinetic substance exchange constant,
   one extracellular volume fraction, and
   at least one further modeling value.

19. The method as claimed in claim 9, wherein the uptake of the at least one radiotracer in the body region of interest is quantified by at least one of
   by taking into account the scattering of photons in the body region of interest,
   in a detector used for the positron emission tomography measurement, and
   by taking into account absorption of photons in the body region of interest.

20. A medical device, comprising:
   an integrated unit configured to record positron emission tomography data and magnetic resonance imaging data for at least one radiotracer in a body region of a patient of interest; and
   a computational unit configured to receive the positron emission tomography data and the magnetic resonance imaging data from the integrated unit, the computational unit being configured to quantify uptake of the at least one radiotracer in the body region of the patient of interest to a positron emission tomography measurement,
      by taking into account at least one permeability information item relating to permeability of at least one blood vessel of the patient determined within the scope of a dynamic contrast-enhanced magnetic resonance imaging measurement, and
      by taking into account differing permeability of an used contrast agent for magnetic resonance imaging and at least one of the permeability of the at least one radiotracer and relaxivity of the contrast agent,
   wherein the quantifying occurs based on data relating to the transfer of the at least one radiotracer from the at least one blood vessel of the patient into tissue surrounding the body region.

21. A non-transitory computer readable medium configured to interact with a computer device, comprising:
   program segments configured to, when executed on the computer device, quantify uptake of at least one radiotracer in a body region of a patient of interest to a positron emission tomography measurement,
      by taking into account at least one permeability information item relating to permeability of at least one blood vessel of the patient determined within the scope of a dynamic contrast-enhanced magnetic resonance imaging measurement, and
      by taking into account differing permeability of an used contrast agent for magnetic resonance imaging and at least one of the permeability of the at least one radiotracer and relaxivity of the contrast agent,
   wherein the quantifying occurs based on data relating to the transfer of the at least one radiotracer from the at least one blood vessel of the patient into tissue surrounding the body region.

\* \* \* \* \*